(12) United States Patent
Scaife et al.

(10) Patent No.: US 6,683,102 B2
(45) Date of Patent: Jan. 27, 2004

(54) METHODS OF USING METAXALONE IN THE TREATMENT OF MUSCULOSKELETAL CONDITIONS

(76) Inventors: Michael Scaife, 13460 Old Winery Rd., Poway, CA (US) 92064; Jaymin Shah, 1092 Dalles Ave., Sunnyvale, CA (US) 94086

( * ) Notice: Subject to any disclaimer, the term of this patent is extended or adjusted under 35 U.S.C. 154(b) by 0 days.

(21) Appl. No.: 10/104,044

(22) Filed: Mar. 25, 2002

(65) Prior Publication Data

US 2003/0216457 A1 Nov. 20, 2003

Related U.S. Application Data

(63) Continuation of application No. 09/998,206, filed on Dec. 3, 2001, now Pat. No. 6,407,128.

(51) Int. Cl.$^7$ ............................................. A61K 31/42
(52) U.S. Cl. ............................................. 514/376
(58) Field of Search ............................... 514/376

(56) References Cited

U.S. PATENT DOCUMENTS

| | | | |
|---|---|---|---|
| 3,062,827 A | 11/1962 | Lunsford | 260/307 |
| 3,993,767 A | 11/1976 | Alphin et al. | 424/272 |
| 4,036,957 A | 7/1977 | Alphin et al. | 424/232 |
| 4,792,449 A | 12/1988 | Ausman et al. | 424/440 |
| 4,820,690 A | 4/1989 | Gregory et al. | 514/12 |
| 4,963,361 A | 10/1990 | Kawazi | 424/443 |
| 5,538,954 A | 7/1996 | Koch et al. | 514/53 |
| 5,840,688 A | 11/1998 | Tso | 514/12 |
| 5,977,175 A | 11/1999 | Lin | 514/558 |
| 5,989,583 A | 11/1999 | Amselem | 424/439 |
| 6,017,932 A | 1/2000 | Singh et al. | 514/321 |
| 6,028,054 A | 2/2000 | Benet et al. | 514/9 |
| 6,099,859 A | 8/2000 | Cheng et al. | 424/464 |
| 6,143,325 A | 11/2000 | Dennis et al. | 424/468 |
| 6,407,128 B1 * | 6/2002 | Scaife et al. | 514/376 |
| 2001/0024659 A1 | 9/2001 | Chen et al. | 424/457 |
| 2002/0009474 A1 | 1/2002 | Adusumilli et al. | 424/405 |

OTHER PUBLICATIONS

Fathie, Kazem, "A second look at a skeletal muscle relaxant: a double–blind study of metaxalone," *Current Therapeutic Research*, vol. 6, No. 11, 1964.

Morey et al., "Metaxalone, A New Skeletal Muscle Relaxant," *Journal A.O.A.* vol. 62, pp. 517–521 (1963).

Elenbaas, "Centrally Acting Oral Skeletal Muscle Relaxants," *Am. J. Hosp. Pharm.* vol. 37, pp. 1313–1323 (1980).

Physicians' Desk Reference, Med. Economics Co. Inc., Oradell NJ, 41$^{st}$ Edition, 1987, p. 827.

"Skeletal Muscle Relaxants (Systemic)," Micromedex, Inc., reported to have been revised Aug. 11, 1995, printed from "http://www.nlm.nih.gov/medilineplus/druginfo/uspdi/202523.html" on Sep. 13, 2002, pp. 1–7.

Kazem Fathie, "Musculoskeletal Disorders and Their Management with a New Relaxant," printed from "http://www.aanos.org/edctn__msk__disordr.htm" (the website of The American Academy of Neurological and Orthopaedic Surgeons) on Sep. 13, 2002, pp. 1–5.

Kazem Fathie, "Musculoskeletal Disorders and Their Management with a New Relaxant," *Clinical Medicine*, Apr. 1965, pp. 678–682.

Lunsford et al., 5–Aryloxymethyl–2–oxazolidinones, J. of Am. Chemical Soc., vol. 82, No. 5, Mar. 1960, pp. 1166–1171.

Physicians' Desk Reference, Med. Economics Co. Inc, Montvale NJ, 55$^{th}$ Edition, 2001, p. 1080.

The Merck Index, 11$^{th}$ edition, (Budavari et al Eds.) Merck & Co., Inc., Rahway NJ, 1989, pp. 933–934.

Complaint for Patent Infringement dated Jan. 2, 2003 and filed on behalf of plaintiff Elan Pharmaceuticals, Inc. in *Elan Pharmaceuticals, Inc. v. Eon Labs, Inc.* CV 03 0006 (RDJ, RLM).

Complaint for Patent Infringement dated Mar. 7, 2003 and filed on behalf of plaintiff Elan Pharmaceuticals, Inc. in *Elan Pharmaceuticals, Inc. v. Corepharma, LLC* CV 031013 (DMC).

U.S. patent application Ser. No. 10/386,113, filed on Mar. 2003, Scaife et al.

U.S. patent application Ser. No. 10/420,804, filed on Apr. 2003, Scaife et al.

* cited by examiner

*Primary Examiner*—Raymond Henley, III

(57) ABSTRACT

A method of increasing the bioavailability of metaxalone by administration of an oral dosage form with food is provided, as well as an article of manufacture comprising an oral dosage form of metaxalone in a suitable container and associated with printed labeling which describes the increased bioavailability of the medication in the container when taken with food.

15 Claims, 1 Drawing Sheet

METHODS OF USING METAXALONE IN THE TREATMENT OF MUSCULOSKELETAL CONDITIONS

This is a continuation of application Ser. No. 09/998,206, filed Dec. 3, 2001, now U.S. Pat. No. 6,407,128, the disclosure of which is incorporated herein by reference.

FIELD OF THE INVENTION

The invention relates to methods for increasing the bioavailability of a medicinal agent, namely metaxalone (5-[(3,5-dimethylphenoxy)methyl]-2 oxazolidinone).

BACKGROUND OF THE INVENTION

Metaxalone (Skelaxin®) has the following chemical structure and name:

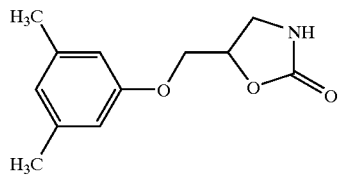

5-[(3,5-dimethylphenoxy)methyl]-2 oxazolidinone

Skelaxin is indicated as an adjunct to rest, physical therapy, and other measures for the relief of discomforts associated with acute, painful musculoskeletal conditions. The mode of action of this drug has not been clearly identified, but may be related to its sedative properties. Metaxalone does not directly relax tense skeletal muscles in man. The commecially available tablet contains: metaxalone, 400 mg along with inert compression tableting excipients.

Metaxalone is further described at Monograph no. 5838 of the Merck Index (Eleventh Addition, Merck & Co., 1989) and is also identified by CAS Registry Number: 1665-48-1. It is also known by the drug code, AHR-438; and the drug product containing it is marketed as Skelaxin® (a trademark of Elan Pharmaceuticals, Inc.).

Preparation of metaxalone is described in Lunsford et al., J. Am. Chem. Soc. 82, 1166 (1960) and U.S. Pat. No. 3,062,827 to Lunsford (Nov. 6, 1962 Assignee A. H. Robins), which is incorporated herein in its entirety by reference. The '827 patent discloses the compound and related species as anticonvulsants and antispasmodics, however, these activities have not been borne out by clinical experience.

Metaxalone is a central nervous system depressant that has sedative and skeletal muscle relaxant effects. Metaxalone is indicated as an adjunct to rest, physical therapy and other measures for the relief of discomforts associated with acute, painful muscoloskeletal conditions. See Skelaxin® monograph, 2001 Physicians' Desk Reference®, Medical Economics Company, Inc. (publisher) Montvale, N.J.

The most frequent reactions to metaxalone include nausea, vomiting, gastrointestinal upset, drowsiness, dizziness, headache, and nervousness or "irritability." Other adverse reactions are: hypersensitivity reaction, characterized by a light rash with or without pruritus; leukopenia; hemolytic anemia; jaundice.

Pharmacokinetic studies have not previously been conducted to date to evaluate the effect of food on the pharmacokinetics of metaxalone. The hydrophobicity of the metaxalone molecule and the dosage amount required for a therapeutic effect both point to probably limited absorption from the gut when administered orally. More oral bioavailability of the drug substance has been sought to increase both speed of onset and amount of therapeutic effect.

SUMMARY OF THE INVENTION

Figure 1:
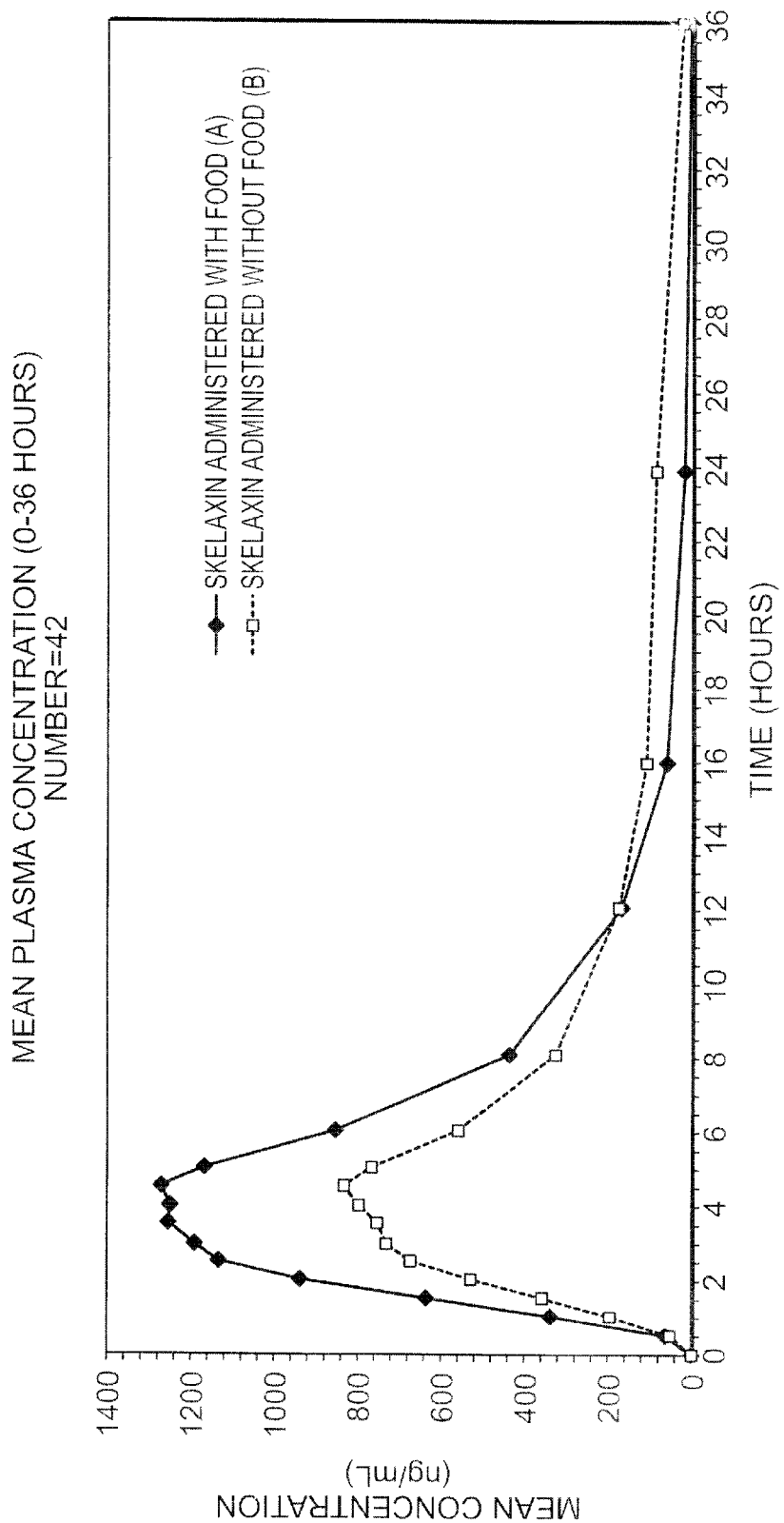
FIG. 1 is a plot of the mean plasma concentration of metaxalone in nanograms per milliliter versus the time elapsed from administration of the dosage form. Two (2) plots are shown for the 400 mg dosage form administered with and without food.

The subject of this invention is the unexpected finding that administration of metaxalone with food increases both the rate and extent of absorption via the oral dosage form in human subjects.

One aspect of this invention is a method of increasing the bioavailability of metaxalone in a human patient receiving metaxalone therapy wherein the metaxalone is contained in a pharmaceutical composition, which method comprises administering a therapeutically effective amount of metaxalone to the patient with food.

Another aspect of the invention is providing a method of increasing rate and extent of metaxalone absorption as measured by the drug concentration attained in the blood stream over time of a patient receiving, the drug in an oral dosage form which method comprises administering a therapeutically effective amount of metaxalone to the patient with food.

Preferably the therapeutic amount is between about 200 mg to about 900 mg, and more preferably between about 400 mg to about 800 mg. Unit dosage forms are preferred.

Preferably the food is a solid food with sufficient bulk and fat content that it is not rapidly dissolved and absorbed in the stomach. More preferably the food is a meal, such as breakfast, lunch or dinner. Advantageously the dosage is administered to the patient between about 30 minutes prior to about 2 hours after eating a meal, most advantageously the dosage is administered within 15 minutes of eating a meal. The terms "without food", "fasted" and "an empty stomach" are defined to mean the condition of not having consumed solid food for about 1 hour prior to until about 2 hours after such consumption.

Yet another aspect of this invention is providing information to prescribing physicians and patients receiving metaxalone therapy useful in maximizing the therapeutic effect of the oral dosage form, by recommending that metaxalone be taken within about half an hour of consuming food.

Another aspect of this invention is an article of manufacture that comprises a container containing a pharmaceutical composition comprising metaxalone wherein the container holds preferably the metaxalone composition in unit dosage form and is associated with printed labeling instructions advising of the differing absorption when the pharmaceutical composition is taken with and without food.

The effect of food on metaxalone absortpion was identified in a study designed to compare the bioavailability of 400 mg of metaxalone in the formulation the drug product Skelaxin® administered to healthy volunteers with and without food.

An objective was to evaluate the bioavailability of metaxalone when administered to subjects with and without food. A single center, single dose, open-label, two-period, randomized, crossover trial in healthy subjects was conducted over a period of approximately 32 days.

The two study drug treatments were as follows:

Treatment A: metaxalone tablet (400 mg) administered with food

Treatment B: metaxalone tablet (400 mg) administered without food

In fed treatment condition A, study drug was taken 15 minutes after the test meal. The test meal was consumed over a 15 minute time period. There was a 6-day washout period between study drug administrations. Seventeen blood samples were collected, starting with baseline (0 hour) and at the following time points: 0.5, 1, 1.5, 2, 2.5, 3, 3.5, 4, 4.5, 5, 6, 8, 12, 16, 24, and 36 hours.

A total of 44 subjects (31 males/13 females) were enrolled and dosed. Only the plasma of subjects who completed the study were assayed and used for the pharmacokinetic analysis.

A single center, single dose, open label, two-period crossover trial was devised for study in healthy subjects. Each administration was a single oral dose of one Skelaxin® 400 mg tablet with or without food. The study drug was administered as follows:

Treatment A: One (1) 400 mg tablet of metaxalone with 240 mL of room temperature water with food: Breakfast was given to the subjects 30 minutes prior to dosing and eaten within a 15 minute period. The dose of study drug was administered to the subjects 15 minutes after the breakfast was finished.

The breakfast consisted of the following:

2 eggs (fried in butter);
2 strips of bacon;
2 slices of toast with butter;
4 ounces of hash brown potatoes;
1 glass whole milk (8 ounces).

Treatment B: 1 tablet of metaxalone) with 240 mL of room temperature water without food. The study drug was administered with 240 mL room temperature water. A mouth check was performed to verify that the subjects swallowed the dose. Subjects were sequentially dosed at 1 minute intervals. The actual time of dosing was recorded on the Master Flow Sheet (refer to the Appendix 16.3.2 Clinical Study Data). Drug administration (1×400 mg capsule) was assisted with 240 mL of room temperature water consumed under direct observation. Immediately after administration of product, the subject's oral cavity was checked to confirm complete medication and fluid consumption. Dosing was completed as scheduled in 42 of 44 subjects.

The drug substance, metaxalone; was dosed in tablet form.

Content: 400 mg; Route: Oral, Batch/Lot No.: SKLWW263F;

Expiration Date: February 03; Manufacturer: West-Ward Pharmaceutical Corp

All pharmacokinetic parameters were analyzed by non-compartmental methods. The following PK parameters were calculated for the two PK profiles and are defined as follows:

Tmax: Time to maximum concentration;

Cmax: Observed maximum concentration;

kel: Slope of terminal linear portion of concentration/time curve;

T½: Half-life of metaxalone calculated as: 0.693/Kel;

AUC(last): Area under the curve to last quantifiable concentration as measured by the trapezoidal rule;

AUC(inf): The AUC value extrapolated to infinity calculated as: AUC(inf)=AUC(last)+C(t)last/Kel where C(t) last is the last measurable concentration.

Statistical Analysis

All statistical analyses were performed using SAS® software version 6.08 or higher. The PK parameters between the two treatments were compared using an appropriate ANOVA model (analysis of variance) that includes term for treatment, sequence, and period effect. Ninety percent confidence interval was computed for the Cmax and AUC values of the fed treatment with fasting as the reference treatment. During the study there were no protocol deviations to confound the pharmacokinetic and bioavailability analyses. Study results were not corrected for drug potency. The individual test results are summarized in table I

TABLE I

Summary of $AUC_{inf}$ and Ln-Transformed $AUC_{inf}$ for Skelaxin ® Administered With Food (A) vs. Skelaxin ® Administered Without Food (B)

| Subj | Seq. | A:With Food (ng/mL) | B:Without Food (ng/mL) | (A − B) | Ratio (A/B) | % Ratio (A/B) *100 | $Log_e$ A Ln(A) | $Log_e$ B Ln(B) | $Log_e$ Ratio Ln (Ratio) |
|---|---|---|---|---|---|---|---|---|---|
| 2 | 1 | 9031 | 9855 | 824 | 0.916 | 91.64 | 9.108 | 9.196 | 0.087 |
| 3 | 2 | 9609 | 13103 | 3494 | 0.733 | 73.33 | 9.170 | 9.481 | 0.310 |
| 4 | 2 | 5011 | 3867 | 1144 | 1.296 | 129.58 | 8.519 | 8.260 | 0.259 |
| 5 | 1 | 3389 | 2530 | 859 | 1.340 | 133.95 | 8.128 | 7.836 | 0.292 |
| 6 | 2 | 10456 | 7302 | 3154 | 1.432 | 143.19 | 9.255 | 8.896 | 0.359 |
| 7 | 2 | 11217 | 11103 | 114 | 1.010 | 101.03 | 9.325 | 9.315 | 0.010 |
| 8 | 2 | 4025 | 3857 | 168 | 1.044 | 104.36 | 8.300 | 8.258 | 0.043 |
| 9 | 2 | 13708 | 8876 | 4832 | 1.544 | 154.44 | 9.526 | 9.091 | 0.435 |
| 11 | 2 | 8122 | 6570 | 1552 | 1.236 | 123.62 | 9.002 | 8.790 | 0.212 |
| 12 | 1 | 6739 | 5470 | 1269 | 1.232 | 123.20 | 8.816 | 8.607 | 0.209 |
| 13 | 2 | 4614 | 4360 | 254 | 1.058 | 105.83 | 8.437 | 8.380 | 0.057 |
| 14 | 1 | 17347 | 13467 | 3880 | 1.288 | 128.81 | 9.761 | 9.508 | 0.253 |
| 15 | 2 | 5488 | 3535 | 1953 | 1.552 | 155.25 | 8.610 | 8.170 | 0.440 |
| 16 | 1 | 12327 | 12025 | 302 | 1.025 | 102.51 | 9.420 | 9.395 | 0.025 |
| 17 | 1 | 4070 | 3320 | 750 | 1.226 | 122.59 | 8.311 | 8.108 | 0.204 |
| 18 | 1 | 5296 | 4365 | 931 | 1.213 | 121.33 | 8.575 | 8.381 | 0.193 |
| 19 | 2 | 8022 | 8271 | 249 | 0.970 | 96.99 | 8.990 | 9.021 | 0.031 |
| 20 | 2 | 2962 | 2874 | 88 | 1.031 | 103.06 | 7.994 | 7.963 | 0.030 |
| 21 | 1 | 9143 | 7173 | 1970 | 1.275 | 127.46 | 9.121 | 8.878 | 0.243 |

TABLE I-continued

Summary of AUC$_{inf}$ and Ln-Transformed AUC$_{inf}$ for
Skelaxin ® Administered With Food (A) vs.
Skelaxin ® Administered Without Food (B)

| Subj | Seq. | A:With Food (ng/mL) | B:Without Food (ng/mL) | (A − B) | Ratio (A/B) | % Ratio (A/B) *100 | Log$_e$ A Ln(A) | Log$_e$ B Ln(B) | Log$_e$ Ratio Ln (Ratio) |
|---|---|---|---|---|---|---|---|---|---|
| 22 | 2 | 11873 | 7742 | 4131 | 1.534 | 153.36 | 9.382 | 8.954 | 0.428 |
| 23 | 1 | 10456 | 9983 | 473 | 1.047 | 104.74 | 9.255 | 9.209 | 0.046 |
| 24 | 1 | 6507 | 5529 | 978 | 1.177 | 117.69 | 8.781 | 8.618 | 0.163 |
| 25 | 2 | 12143 | 10272 | 1871 | 1.182 | 118.21 | 9.405 | 9.237 | 0.167 |
| 26 | 1 | 4519 | 5391 | 872 | 0.838 | 83.82 | 8.416 | 8.592 | 0.176 |
| 27 | 1 | 5208 | 5061 | 147 | 1.029 | 102.90 | 8.558 | 8.529 | 0.029 |
| 28 | 2 | 5197 | 5012 | 185 | 1.037 | 103.69 | 8.556 | 8.520 | 0.036 |
| 29 | 1 | 10355 | 11601 | 1246 | 0.893 | 89.26 | 9.245 | 9.359 | 0.114 |
| 30 | 1 | 7350 | 6452 | 898 | 1.139 | 113.92 | 8.902 | 8.772 | 0.130 |
| 31 | 1 | 7899 | 7677 | 222 | 1.029 | 102.89 | 8.974 | 8.946 | 0.029 |
| 32 | 2 | 6719 | 4440 | 2279 | 1.513 | 151.33 | 8.813 | 8.398 | 0.414 |
| 33 | 2 | 11295 | 11316 | 21 | 0.998 | 99.81 | 9.332 | 9.334 | 0.002 |
| 34 | 2 | 13357 | 13580 | 223 | 0.984 | 98.36 | 9.500 | 9.516 | 0.017 |
| 35 | 2 | 10710 | 10138 | 572 | 1.056 | 105.64 | 9.279 | 9.224 | 0.055 |
| 36 | 1 | 19077 | 19329 | 252 | 0.987 | 98.70 | 9.856 | 9.869 | 0.013 |
| 37 | 1 | 6727 | 4454 | 2273 | 1.510 | 151.03 | 8.814 | 8.402 | 0.412 |
| 38 | 2 | 19024 | 9934 | 9090 | 1.915 | 191.50 | 9.853 | 9.204 | 0.650 |
| 39 | 1 | 3060 | 3284 | 224 | 0.932 | 93.18 | 8.026 | 8.097 | 0.071 |
| 40 | 1 | 5188 | 4203 | 985 | 1.234 | 123.44 | 8.554 | 8.344 | 0.211 |
| 41 | 1 | 7273 | 6574 | 699 | 1.106 | 110.63 | 8.892 | 8.791 | 0.101 |
| 42 | 2 | 3958 | 3642 | 316 | 1.087 | 108.68 | 8.283 | 8.200 | 0.083 |
| 43 | 1 | 8837 | 4642 | 4195 | 1.904 | 190.37 | 9.087 | 8.443 | 0.644 |
| 44 | 2 | 11427 | 11935 | 508 | 0.957 | 95.74 | 9.344 | 9.387 | 0.043 |

Differences were declared to be significant at the 5% level. The ratio of the geometric means for the ln-transformed data and the corresponding 90% confidence intervals were calculated for AUC(last), AUC(inf), and Cmax. The calculations for the confidence intervals used the least squares means (LSMEANS) and the standard error of the estimate, both generated by the SAS® software.

The lower limit of quantitation for metaxalone was 10 ng/mL. For statistical analysis, subject sample values below the lower limit of quantitation were reported as zero.

Tables IIa and IIb summarize the results of the analyses performed on the pharmacokinetic parameters obtained from the fed and fasted states.

TABLE IIa

| Metaxalone | AUC (last) | AUCinf | Cmax |
|---|---|---|---|
| Treatment A Geometric Mean | 7525.00 | 7630.53 | 1536.23 |
| Treatment B Geometric Mean | 6094.12 | 665.24 | 865.34 |
| % Ratio | 123.48 | 115.35 | 177.53 |
| 90% Confidence Interval | (116.40, 130.99) | (109.24, 121.80) | (156.62, 201.23) |

TABLE IIb

| Metaxalone | AUC (last) | AUCinf | Cmax | Tmax | T1/2 |
|---|---|---|---|---|---|
| Treatment A Least Squares Mean | 8439.62 | 8541.31 | 1773.61 | 4.29 | 2.37 |
| Treatment B Least Squares Mean | 6961.81 | 7478.90 | 983.37 | 3.32 | 9.04 |

With a 5% significance level, the ANOVA detected statistically significant differences between treatments for ln-transformed AUC(last), AUCinf, and Cmax, as well as for untransformed AUC(last), AUC(inf), Cmax, Tmax, T½, and Kel. The ANOVA detected no statistically significant differences between periods or between sequences.

The mean T$_{1/2}$ (half-life) of metaxalone with food and without food were 2.37 and 9.04 hours respectively. The exact reason for this discrepancy is unclear. However, the AUC last is outside the confidence interval, indicating a significant food effect.

Ratio (A/B) of geometric means for AUC(last), AUC(inf) and Cmax were 123.48%, 115.35% and 177.53%, respectively demonstrating that metaxalone administered with food increased both its rate and extent of absorption.

ANOVA detected statistically significant differences between treatments for ln-transformed AUC(last), AUC (inf), and Cmax, as well as for untransformed AUC(last), AUC(inf),Cmax, T½, and Kel. ANOVA did not detect any statistically significant differences between treatments for untransformed Tmax.

Conclusion: Administration with food increases both the rate and extent of absorption of metaxalone 400 mg tablets when administered as a single dose. The bioavailability of metaxalone 400 mg tablets increased when administrated with food.

Article of Manufacture

The article of manufacture comprises a container holding an immediate release pharmaceutical composition suitable for oral administration of metaxalone in combination with printed labeling instructions providing a discussion of when a particular dosage form should be administered with food and when it should be taken on an empty stomach. The composition will be contained in any suitable container capable of holding and dispensing the dosage form and which will not significantly interact with the composition and will further be in physical relation with the appropriate labeling advising that an immediate release tablet dosage form has less somnolence associated with its use if taken on an empty stomach and an immediate release multiparticulate dosage form has less somnolence associated with its use if taken with food. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

While the invention has been described by discussion of embodiments of the invention and non-limiting examples thereof, one of ordinary skill in the art may, upon reading the specification and claims, envision other embodiments and variations which are also within the intended scope of the invention and therefore the scope of the invention shall only be construed and defined by the scope of the appended claims.

We claim:

1. A method of using metaxalone in the treatment of musculoskeletal conditions comprising:
   providing the patient with a therapeutically effective amount of metaxalone; and
   informing the patient that the administration of metaxalone with food results in an increase in at least one of C(max) and AUC(last) of metaxalone compared to administration without food.

2. The method according to claim 1, wherein therapeutically effective amount of metaxalone comprises 200 mg to 900 mg of metaxalone.

3. The method according to claim 2, wherein the therapeutically effective amount of metaxalone comprises 400 mg to 800 mg of metaxalone.

4. The method according to claim 1, wherein the metaxalone is provided in tablet form.

5. The method according to claim 4, wherein the tablet is in unit dosage form.

6. A method of using metaxalone in the treatment of musculoskeletal conditions comprising:
   informing a patient with musculoskeletal conditions that the administration of a therapeutically effective amount of metaxalone with food results in an increase in at least one of C(max) and AUC(last) of metaxalone compared to administration without food.

7. A method of using metaxalone in the treatment of musculoskeletal conditions comprising altering the oral bioavailability of metaxalone by:
   obtaining metaxalone from a container providing information that administration of metaxalone with food increases at least one of C(max) and AUC(last) of metaxalone compared to administration without food, and
   ingesting the metaxalone with food.

8. A method of using metaxalone in the treatment of musculoskeletal conditions comprising:
   administering to a patient in need of treatment a therapeutically effective amount of metaxalone, with food, wherein the administration of the metaxalone with food results in an increase in at least one of C(max) and AUC(last) of metaxalone as compared to administration of metaxalone in a fasted state; and
   informing the patient that the administration of a therapeutically effective amount of metaxalone in a pharmaceutical composition with food results in an increase in at least one of C(max) and AUC(last) of metaxalone compared to administration in a fasted state.

9. The method according to claim 8, wherein the metaxalone is from a container with printed labeling advising that administration with food results in an increase in at least one of C(max) and AUC(last) of metaxalone compared to administration in a fasted state.

10. The method according to claim 9, wherein the metaxalone is provided in tablet form.

11. The method according to claim 10, wherein the metaxalone is provided in 400 mg tablet form.

12. The method according to claim 9, wherein the printed labeling advises that the administration of the metaxalone with food results in an increase in the C(max) of 177.5%.

13. The method according to claim 9, wherein the printed labeling advises that the administration of the metaxalone with food results in an increase in the AUC(last) of 123.5%.

14. The method according to claim 9, wherein the printed labeling further advises that the administration of the metaxalone with food results in an increase in AUC(inf) of 115.4%.

15. The method according to claim 8, wherein the metaxalone is provided in 400 mg tablet form, and the printed labeling advises that administration of metaxalone with food results in an increase in C(max), AUC(last), and AUC(inf), of 177.5%, 123.5%, and 115.4%, respectively, compared to administration of metaxalone in a fasted state.

* * * * *

UNITED STATES PATENT AND TRADEMARK OFFICE
CERTIFICATE OF CORRECTION

PATENT NO. : 6,683,102 B2
DATED : January 27, 2004
INVENTOR(S) : Scaife et al.

It is certified that error appears in the above-identified patent and that said Letters Patent is hereby corrected as shown below:

<u>Title page,</u>
Item [56], Reference Cited, OTHER PUBLICATIONS, the following reference should be included:
-- Clinical Study Report, ELN151607-105 dated April 16, 2003 --

Signed and Sealed this

Eleventh Day of May, 2004

JON W. DUDAS
*Acting Director of the United States Patent and Trademark Office*